United States Patent [19]

Salzmann

[11] Patent Number: 4,491,580
[45] Date of Patent: Jan. 1, 1985

[54] AZABICYCLO[2.1.0] ANTIBIOTICS

[75] Inventor: Thomas N. Salzmann, North Plainfield, N.J.

[73] Assignee: Merck & Co., Inc., Rahway, N.J.

[21] Appl. No.: 365,068

[22] Filed: Apr. 2, 1982

[51] Int. Cl.$^3$ ................. C07D 205/08; C07D 205/12; A61K 31/395
[52] U.S. Cl. ............................... 424/244; 260/239 A
[58] Field of Search ................... 260/239 AL; 424/244

[56] References Cited
PUBLICATIONS

Trifonov et al., Monat Chem. 111, 1117-23 (1980).

*Primary Examiner*—Mark L. Berch

*Attorney, Agent, or Firm*—Raymond M. Speer; Daniel T. Szura

[57] ABSTRACT

Disclosed are azabicyclo[2.1.0] antibiotics (I) and their pharmaceutically acceptable salts and esters which are useful as antibiotics.

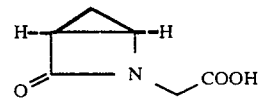

I

Also disclosed are processes for the preparation of such compounds; pharmaceutical compositions comprising such compounds; and methods of treatment comprising administering such compounds and compositions when an antibiotic effect is indicated.

4 Claims, No Drawings

AZABICYCLO[2.1.0] ANTIBIOTICS

BACKGROUND OF THE INVENTION

This invention relates to azabicyclo[2.1.0]antibiotics (I) and the pharmaceutically acceptable salt and ester derivatives thereof which are useful as antibiotics:

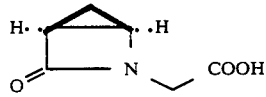

This invention also relates to the carboxyl derivatives of I which are antibiotics and which may be represented by the following generic structure (I):

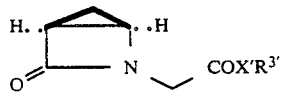

wherein X' is oxygen, sulphur or NR' (R'=H or lower alkyl having 1-6 carbon atoms); and $R^{3'}$ is, hydrogen, or, inter alia is representatively selected to provide the pharmaceutically acceptable salt, ester, anhydride ($R^{3'}$ is acyl), and amide moieties known in bicyclic β-lactam antibiotic art; $R^3$ may also be a readily removable blocking group. The definition of $R^{3'}$ is given in greater detail below.

This invention also relates to processes for the preparation of such compounds I; pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly, the search for new antibiotics continues.

Thus, it is an object of the present invention to provide a novel class of antibiotics which are useful in animal and human therapy and in inanimate systems. These antibiotics are active against a broad range of pathogens which representatively include both Gram positive bacteria such as *S. aureus, Strep. pyogenes,* and *B. subtilis,* and Gram negative bacteria such as *E. coli,* Pseudomonas, *Proteus morganii,* Serratia, and Klebsiella. Further objects of this invention are to provide chemical processes for the preparation of such antibiotics and their nontoxic, pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

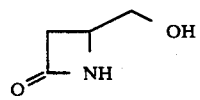

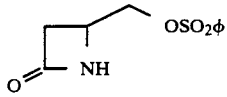

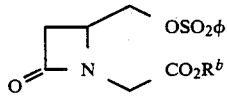

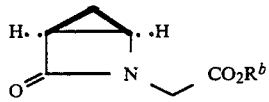

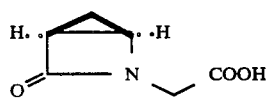

In words relative to the above diagram, starting material 1 is known; see, for example, U.S. Pat. No. 4,174,316 (issued Nov. 13, 1979). The transformation 1 to 2 is accomplished by treating 1 with $\phi SO_2Cl$ in the presence of a base such as triethylamine, diisopropylethylamine, pyridine, 4-dimethylaminopyridine or the like, in a solvent such as methylene chloride, pyridine, tetrahydrofuran or the like, at a temperature of from −50° C. to 50° C. for from 1 to 48 hours.

The transformation 2 to 3 is accomplished by treating 2 with sodium hydride, potassium hydride, lithium diisopropyl amide, or the like, in a solvent such as tetrahydrofuran, dimethoxyethane, ether, or the like, in the presence of $X^a CH_2 CO_2 R^b$ at a temperature of from −78° to 25° C. for from 0.5 to 24 hours; $X^a$ is iodo, bromo, tosylate; $R^b$ is a protecting group such as benzyl, p-nitrobenzyl, benzhydryl, or the like, or a pharmaceutically acceptable ester moiety.

The transformation 3 to 4 is accomplished by treating 3 with 2.0 to 4.0 equivalents of lithium hexamethyldisilazide, lithium diisopropylamide or the like, in a solvent such as tetrahydrofuran, dimethoxyethane, ether, or the like, at a temperature of from −78° to 25° C. for from 0.2 to 4 hours.

The final deblocking step 4 I is accomplished by conventional procedures such as solvolysis or hydrogenation. Typically 4 in a solvent such as dioxane-water-ethanol, tetrahydrofuran-aqueous sodium bicarbonate, tetrahydrofuran-aqueous dipotassium hydrogen phosphate-isopropanol or the like is treated under a hydrogen pressure of from 1 to 4 atmospheres in the presence of a hydrogenation catalyst such as palladium on charcoal, palladium hydroxide, platinum oxide, or the like at a temperature of from 0° to 50° C. for from 0.25 to 4 hours to provide I. Photolysis, when $R^b$ is a group such as o-nitrobenzyl, for example, may also be used for deblocking.

As noted above, the compounds of the present invention may also generally be represented by the following structural formula:

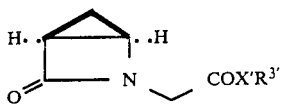

wherein X' is oxygen, sulfur or NR' (R' is hydrogen or loweralkyl having from 1 to 6 carbon atoms); and $R^{3'}$ is hydrogen, or, inter alia, is representatively selected to provide the pharmaceutically acceptable salt, ester, anhydride ($R^{3'}$ is acyl), and amide moieties known in the bicyclic β-lactam antibiotic art; $R^{3'}$ may also be a readily removable blocking group.

IDENTIFICATION OF THE RADICAL —COX'R$^{3'}$

In the generic representation of the compounds of the present invention (I, above), the radical represented by —COX'R$^{3'}$ is, inter alia, —COOH (X' is oxygen and $R^{3'}$ is hydrogen) and all radicals known to be effective as pharmaceutically acceptable ester, anhydride ($R^{3'}$ is acyl) and amide radicals in the bicyclic β-lactam antibiotic art, such as the cephalosporins and penicillins and nuclear analogues thereof.

Suitable, but representative, blocking esters $R^{3'}$ (X=O) include those selected from the following list which is representative:

(i) $R^{3'}=CR^aR^bR^c$ wherein at least one of $R^a$, $R^b$, and $R^c$ is an electrondonor, e.g., p-methoxyphenyl. The remaining $R^a$, $R^b$ and $R^c$ groups may be hydrogen or organic substituting groups. Suitable ester groups of this type include p-methoxybenzyloxycarbonyl.

(ii) $R^{3'}=CR^aR^bR^c$ wherein at least one of $R^a$, $R^b$ and $R^c$ is an electron-attracting group, e.g., p-nitrophenyl, trichloromethyl, and o-nitrophenyl. Suitable esters of this type include p-nitrobenzyloxycarbonyl, and 2,2,2-trichloroethoxycarbonyl.

(iii) $R^{3'}=CR^aR^bR^c$ wherein at least two of $R^a$, $R^b$ and $R^c$ are hydrocarbon such as alkyl, e.g., methyl or ethyl, or aryl, e.g., phenyl and the remaining $R^a$, $R^b$ and $R^c$ group, if there is one, is hydrogen. Suitable esters of this type include t-butyloxycarbonyl, diphenylmethoxycarbonyl and triphenylmethoxycarbonyl.

Silyl esters. This category of blocking groups, may conveniently be prepared from a halosilane of the formula: $R_3^4SiX'$ wherein X' is a halogen such as chloro or bromo and $R^4$ is alkyl, having 1–6 carbon atoms, phenyl, or phenylalkyl.

Pharmaceutically acceptable carboxyl derivatives of the present invention are those derived by reacting I with alcohols, acylating reagents and the like. For example, esters and amides of interest are the above-listed starting materials and final products having the —COX'R$^{3'}$ group at the 3-position; wherein X' is oxygen, sulfur or NR' (R' is H or $R^{3'}$), and $R^{3'}$ is alkyl having 1–6 carbon atoms, straight or branched, such as methyl, ethyl, t-butyl, and the like; carbonylmethyl, including phenacyl; aminoalkyl including 2-methylaminoethyl, 2-diethylaminoethyl; alkanoyloxyalkyl wherein the alkanoyloxy portion is straight or branched and has 1–6 carbon atoms and the alkylportion has 1–6 carbon atoms, such as pivaloyloxymethyl; haloalkyl wherein halo is chloro, and the alkyl portion is straight or branched having 1–6 carbon atoms, e.g., 2,2,2-trichloroethyl; alkenyl having 1–4 carbon atoms such as 2-propenyl, 3-butenyl, and 4-butenyl; aralkyl and lower alkoxyl- and nitro-substituted aralkyl such as benzyl, benzhydryl, o-nitrobenzyl, p-methoxybenzyl, and p-nitrobenzyl, phthalidyl; benzyloxyalkyl having 8–10 carbon atoms such as benzyloxymethyl, and (4-nitro)benzyloxymethyl.

In addition to the esters (and thio esters) listed above, amides are also embraced by the present invention, i.e., wherein X' is the

group. Representatives of such amides are those wherein R' is selected from the group consisting of hydrogen and alkyl such as methyl and ethyl.

The most preferred —COX'R$^{3'}$ radicals of the present invention are those wherein (relative to Structure I above), X' is oxygen and $R^{3'}$ is hydrogen; loweralkyl having 1–4 carbon atoms; lower alkenyl such as 3-methylbutenyl, 4-butenyl and the like; benzyl and substituted benzyl such as p-nitrobenzyl; pivaloyloxymethyl, 3-phthalidyl; and phenacyl.

The compounds of the present invention (I) are valuable antibiotics active against various Gram-positive and Gram-negative bacteria and accordingly find utility in human and veterinary medicine. Representative pathogens which are sensitive to antibiotics I include: *Straphylococcus aureus, Escherichia coli, Klebsiella pneumoniae, Bacillus subtilis, Salmonella typhosa Pseudomonas* and *Bacterium proteus.* The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The products of this invention may be used in any of a variety of pharmaceutical preparations. They may be employed in capsule, powder form, in liquid solution, or in suspension. They may be administered by a variety of means; those of principal interest include: orally, topically or parenterally by injection (intravenously or intramuscularly).

Such tablets and capsules, designed for oral administration, may be in unit dosage form, and may contain conventional excipients, such as binding agents, for example, syrup, acacia, gelatin, sorbitol, tragacanth, or polyvinylpyrrolidone; fillers, for example, lactose, sugar, cornstarch, calcium phosphate, sorbitol, or glycerine; lubricants, for example, magnesium stearate, talc, polyethylene glycol, silica; disintegrants, for example, potato starch, acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, such as cocoa butter or other glycerides.

Compositions for injection, the preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water.

The compositions may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semi-solid form. Topical applications may be formulated in hydrophobic or hydrophilic bases as ointments, creams, lotions, paints, or powders.

The dosage to be administered depends to a large extent upon the condition and size of the subject being treated—as well as the route and frequency of administration—the parenteral route by injection being preferred for generalized infections. Such matters, however, are left to the routine discretion of the therapist according to principles of treatment well known in the antibiotic art. In general, a daily dosage consists of from about 5 to about 600 mg of active ingredient per kg. of body weight of the subject in one or more treatments per day. A preferred daily dosage for adult humans lies in the range of from about 10 to 240 mg. of active ingredient per kg. of body weight. Another factor influencing the precise dosage regimen, apart from the nature of the infection and peculiar identity of the individual being treated, is the molecular weight of the chosen species of this invention (I).

The compositions for human delivery per unit dosage, whether liquid or solid, may contain from 0.1% to 99% of active material, the preferred range being from about 10–60%. The composition will generally contain from about 15 mg. to about 1500 mg. of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution. For zwitterionic species described under Structure I, the pH of such solutions typically will correspond to the zwitterionic point; however, consideration of individual properties of solubility and stability may require such aqueous solutions to have a pH other than that of the zwitterionic point, for example in the range of 5.5 to 8.2.

In the foregoing word description of the above, schematic reaction diagram for the total synthesis of the desired cyclonocarbicin antibiotics, it is to be understood that there is considerable latitude in selection of precise reaction parameters. Suggestion of this latitude and its breadth is generally indicated by the enumeration of equivalent solvent systems, temperature ranges, protecting groups, and range of identities of involved reagents. Further, it is to be understood that the presentation of the synthetic scheme as comprising distinct steps in a given sequence is more in the nature of a descriptive convenience than as a necessary requirement; for one will recognize that the mechanically dissected scheme represents a unified scheme of synthesis and that certain steps, in actual practice, are capable of being merged, conducted simultaneously, or effected in a reverse sequence without materially altering the progress of synthesis.

The following examples recite a precise scheme of total synthesis. It is to be understood that the purpose of this recitation is to further illustrate the total synthesis and not to impose any limitation. Temperature is in °C.

EXAMPLE 1

Preparation of Sodium
(1R,4S)-2-azabicyclo[2,1,0]-pentan-3-one

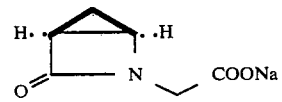

Preparation of (S)-4-Benzenesulfonyloxymethyl azetidin-2-one

Triethylamine (5.74 g, 56.8 mmol) was added by syringe to a solution of (S)-4-hydroxymethylazetidin-2-one (3.79 g, 37.5 mmol) and benzenesulfonylchloride (10.0 g, 56.8 mmol) in dry methylene chloride (38 ml) at 0° C. The resulting mixture was stirred at 0° C. for 4 hrs., then diluted with methylene chloride (100 ml), washed with water (50 ml) and brine (25 ml) and dried over magnesium sulfate. Solvents were removed in vacuo to give a brown gum which was chromatographed on silica gel (100 g) (ethylacetate) to yield 6.6 g (73%) of (S)-4-benzenesulfonyloxymethyl azetidin-2-one as a white solid, m.p. 102°–105° C.

(S)-1-Benzyloxycarbonylmethyl-4-benzenesulfonyloxymethylazetidin-2-one

A solution of (S)-4-benzenesulfonyloxymethylazetidin-2-one (241 mg, 1.00 mmol) and benzylbromoacetate (341 mg, 1.5 mmol) in freshly distilled tetrahydrofuran (5 ml) was added slowly by syringe to a suspension of sodium hydride (58 mg of 50%, 1.2 mmol) in tetrahydrofuran (10 ml) at 0° C. for 5 hr., then was poured into a separatory funnel containing ether (100 ml) and 10% aqueous hydrochloric acid solution (25 ml). The organic phase was separated, washed with water and brine and dried over magnesium sulfate. Removal of solvents in vacuo gives a yellow oil which was chromatographed on three 1000µ silical gel plates (ether) to yield 214 mg (55%) of (S)-1-benzyloxycarbonylmethyl-4-benzenesulfonyloxymethylazetidin-2-one. NMR (CDCl$_3$) 7.2–8.0 (10H, m, aromatics), 5.2 (2H, S, CH$_2$O), 3.8–4.5 (5H, m, N-CH$_2$, CH$_2$O—, bridgehead), 3.1 (1H, dd, J=15, 3.9, H3), 2.65 (1H, dd, J=15, 2).

1(R,4S)-2-Benzyloxycarbonylmethyl-2-azabicyclo[2,1,0]pentan-3-one n-Butyllithium (248)11 of 2.3M, 0.57 mmol) was added via syringe to a solution of hexamethyldisilazane (92 mg. 0.57 mmol) in freshly distilled tetrahydrofuran (3 ml) at −78° C. The resulting solution was stirred at −78° C. for 15 min prior to the addition of a solution of (S)-1-benzyloxycarbonylmethyl-4-benzene-sulfonyloxymethylazetidin-2-one (100 mg, 0.26 mmol) in tetrahydrofuran (1 ml). The reaction mixture was stirred at −78° C. for 1 hr., then was allowed to warm to 0° C. over about 30 min. After stirring an additional 15 min at 0° C. the reaction was quenched by addition of saturated aqueous ammonium chloride (5 ml), diluted with ether (50 ml) and washed with water (20 ml) and brine (10 ml). The organic phase was dried over magnesium sulfate and concentrated in vacuo to yield a yellow oil which was chromatographed on a 1000μ silica gel plate (ether) to yield 24.6 mg (41%) of (1R, 4S)-2-benzyloxycarbonylmethyl-2-azabicyclo[2.1,0]pentan-3-one. NMR (CHDl₃) 7.33 (5H,S, aromatic), 5.15 (2H,S,CH₂—O), 3.8 (2H, ABq, CH₂CO₂—), 3.9 (1H, ddd, J=1,3,4H1), 2.5 (1H, ddd, J=2,4,6.3, H4), 2.2 (1H, ddd, J=1,2,5,H5) 1.8 (1H, ddd, J=3,5,6,3,H5).

Sodium (1R,4S)-2-azabicyclo[2,1,0]pentan-3-one-2-carboxylate

A mixture of (1R,4S)-2-benzyloxycarbonylmethyl-2-azabicyclo[2,1,0]pentan-3-one (21 mg, 0.091 mmol), 10% Pd/C (10 mg) and sodium bicarbonate (7.6 mg, 0.91 mmol) in tetrahydrofuran (3 ml) water (1 ml) was hydrogenated at 40 psi on the Parr shaker for 1 hr. The mixture was then filtered and the solid residue was washed with deionized water. The combined filtrate and washings were extracted twice with ether (10 ml) and the aqueous phase was concentrated in high vacuum to a volume of 3.5 ml. This solution was applied to a ½" disc (total product content on disc 400 μg) which was incubated on a Staph. aureus MB 108 plate at 37° C. for 60 hrs. This results in a 50 mm zone of inhibition.

EXAMPLE 2

Preparation of Pharmaceutical Compositions

One such unit dosage form is prepared by mixing 120 mg of compound A (compound of Example 1) with 20 mg of lactose and 5 mg of magnesium stearate and placing the 145 mg mixture into a No. 3 gelatin capsule. Similarly, by employing more of the active ingredient and less lactose, other dosage forms can be put up in No. 3 gelatin capsules, and, should it be necessary to mix more than 145 mg of ingredients together, larger capsules such as compressed tablets and pills can be prepared. The following examples are illustrative of the preparation of pharmaceutical formulations:

| TABLET | PER TABLET |
|---|---|
| Compound A | 125 mg. |
| Cornstarch, U.S.P. | 6 mg. |
| Dicalcium Phosphate | 192 mg. |
| Lactose, U.S.P. | 190 mg. |
| Magnesium Stearate | Balance/800 mg. |

The active ingredient is blended with dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and magnesium stearate is added and the mixture is compressed into tablets, approximately 0.5 inch in diameter each weighing 800 mg.

| | PER TABLET |
|---|---|
| PARENTERAL SOLUTION | |
| Ampoule: | |
| Compound A | 500 mg. |
| Diluent: Sterile Water for Injection | 2 cc. |
| OPHTHALMIC SOLUTION | |
| Compound A | 100 mg. |
| Hydropropylmethyl Cellulose | 5 mg. |
| Sterile Water | to 1 ml. |
| OTIC SOLUTION | |
| Compound A | 100 mg. |
| Benzalkonium chloride | 0.1 mg. |
| Sterile Water | to 1 ml. |
| TOPICAL OINTMENT | |
| Compound A | 100 mg. |
| Polyethylene Glycol 4000 U.S.P. | 400 mg. |
| Polyethylene Glycol 400 U.S.P. | 1.0 gram |

What is claimed is:

1. A compound of the structure

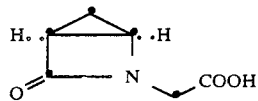

and pharmaceutically acceptable salts and esters thereof, said salts and esters being those known in the bicyclic β-lactam antibiotic art.

2. An antibacterial method of treatment comprising administering to an animal or human a therapeutically effective amount of a compound of claim 1 together with a pharmaceutically acceptable carrier.

3. An antibacterial pharmaceutical composition comprising a therapeutically effective amount of a compound of claim 1 and a pharmaceutically acceptable carrier therefor.

4. The compound of claim 1 having the structure

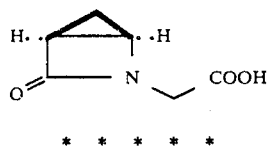

* * * * *